United States Patent [19]
Kempf et al.

[11] Patent Number: 5,866,316
[45] Date of Patent: Feb. 2, 1999

[54] PHOTODYNAMIC INACTIVATION OF ENVELOPED VIRUSES USING BUCKMINSTERFULLERENE

[75] Inventors: Christoph Kempf, Detligen; Fabian Käsermann, Burgdorf, both of Switzerland

[73] Assignee: Rotkreuzstiftung Zentrallaboratorium Blutspendedienst SRK, Bern, Switzerland

[21] Appl. No.: 813,635

[22] Filed: Mar. 7, 1997

[30] Foreign Application Priority Data

Mar. 8, 1996 [EP] European Pat. Off. .............. 96810146

[51] Int. Cl.$^6$ ................................. A01N 1/02; C12N 7/06
[52] U.S. Cl. .................................. 435/2; 435/238
[58] Field of Search .......................... 435/2, 238

[56] References Cited

U.S. PATENT DOCUMENTS

| | | |
|---|---|---|
| 4,775,625 | 10/1988 | Sieber . |
| 5,466,587 | 11/1995 | McElligott et al. . |
| 5,571,666 | 11/1996 | Floyd et al. ................ 435/2 |

FOREIGN PATENT DOCUMENTS

| | | |
|---|---|---|
| 515194A2 | 5/1992 | European Pat. Off. . |
| WO92/11059 | 7/1992 | WIPO . |

OTHER PUBLICATIONS

Nagano et al., "Comparaison of Singlet Oxygen Production Efficiency of C60 with Other Photosensitizers, Based on 1268nm Emission", Chem. Pharm. Bull. 42 (11) : 2291–94 (1994).

Muller–Breitkreutz et al., "Inactivation of viruses by chemically and photochemically generated singlet molecular oxygen", J. Photochem. Photobiol. B,Biology 30 (1) :63–70 (1995).

North et al., "Photosensitizers as Virucidal Agents", J. Photochem. Photobiol. B: Biol., 17:99–108 (1993).

Suomela, "Inactivation of Viruss in Blood and Plasma Products" Transfusion Medicine Reviews, VII (1):42–57 (1993).

Mohr et al., "Photodynamic Virus Inactivation of Blood Components", Immunol. Invest, 1995 Jan.; 24(1–2):73–85.

*Primary Examiner*—Sandra E. Saucier
*Attorney, Agent, or Firm*—Jacobson, Price, Holman & Stern, PLLC

[57] ABSTRACT

In a process for the inactivation of enveloped viruses in a biological fluid buckminsterfullerene ($C_{60}$) is used as a photosensitizer. In a photodynamic processes singlet oxygen is generated which is the active agent for the inactivation of viruses present in the fluid. The process comprises the steps of (a) contacting of a solution or dispersion of material derived from the human body or from the bodies of animals with buckminsterfullerene as a photosensitizer, of (b) saturating the solution or dispersion with oxygen; and of (c) irradiating the solution or dispersion with visible or invisible light for activating the oxygen into the singlet state until viruses contained in the solution or dispersion are inactivated. This virus inactivation is specially suitable for protein solutions, e.g. bovine serum albumin, BSA or plasma products of human origin.

27 Claims, 2 Drawing Sheets

PHOTODYNAMIC INACTIVATION OF ENVELOPED VIRUSES USING BUCKMINSTERFULLERENE

This invention relates to a process for inactivating viruses in a solution or dispersion of material derived from the human body or from the bodies of animals with the use of buckminsterfullerene ($C_{60}$; CAS Nr. 99685-96-8) as a singlet oxygen-generating photosensitizer.

Photoinactivation by dyes has been known to be effective on enveloped viruses in blood. Dyes like phthalocyanines, merocyanines, porphyrin derivatives, hypericin, rose bengal and methylene blue have been shown to inactivate enveloped viruses [for reviews see North, J., Neyndorff, H. and Levy, J. G.: *J. Photochem. Photobiol.*, 17 (1993) 99–108; Suomela, H.: *Transf. Medic. Rev.* 7 (1993) 42–57].

The photosensitizer is first excited to the short-lived singlet state following the absorption of light. The singlet state of the sensitizer is converted into the triplet state via an intersystem crossing mechanism, which results in more stable and longer living species. Usually, photosensitization occurs via the triplet state. The triplet state of the sensitizer can transfer its energy to the ground state of oxygen resulting in highly reactive singlet oxygen ($^1O_2$; Type II pathway).

Up to today, a variety of dyes have been tested concerning their capacity to inactivate viruses in biological fluids by singlet oxygen generation. An inherent property of most dyes used to date was their water solubility. Thus it becomes extremely difficult to remove such dyes from the reaction mixture. Many of these dyes or newly formed photoproducts thereof might be toxic or are known mutagens. No long term studies are available regarding the application to humans or animals for the most dyes which might be used in the future. Thus total removal of these dyes from biological fluids will be in most cases a prerequisite. In the production of blood plasma products there exists a single established method of photoinactivation of viruses, namely the treatment of fresh frozen plasma with methylene blue and visible light [Mohr, H., Lambrecht, B., and Selz, A.: *Immunological-Investigations* 24 (1995) 73–85]. However, this method is—like all other known photoinactivation methods—far from being applicable to cellular products such as erythrocytes or thrombocytes. At present, in methylene blue treated fresh frozen plasma, the dye remains with the product.

The object of the present invention is therefore a process for inactivating viruses using singlet oxygen formed in the presence of a photosensitizer which is not toxic and which can easily and completely be removed from a solution or dispersion comprising material derived from the human body or from the bodies of animals.

According to the invention the problem was solved by contacting a solution or dispersion comprising material derived from the human body or from the bodies of animals with buckminsterfullerene as a photosensitizer; saturating the solution or dispersion with oxygen; and irradiation of the solution or dispersion with visible or invisible light for activating the oxygen into the singlet state until viruses contained in the solution or dispersion are inactivated.

The all carbon molecule buckminsterfullerene ($C_{60}$) was well studied during the last years [Kroto, H. W., Allaf, A. W. and Balm, S. P.: *Chem. Rev.* 91 (1991) 1213–1235]. The photochemical and photophysical properties of buckminsterfullerene have recently received intensive attention. The triplet state of $C_{60}$ sensitizes the formation of singlet oxygen in high yields (quantum yield=0.96, at 535 nm) as measured by $^1O_2$ luminescence at 1268 nm [Arbogast, J. W., Darmanyan, A. P., Foote, C. S., Rubin, Y., Diederich, F. N., Alvarez, M. M., Anz, S. J., and Whetten, R. L.: *J. Phys. Chem.* 95 (1991) 11–12; Nagano, T., Arakane, K., Ryu, A., Masunaga, T., Shinmoto, K., Mashiko, S., and Hirobe, M.: Chem. Pharm. Bull. 42 (1994) 2291–2294]. Therefore $C_{60}$ is a potent generator of singlet oxygen and is used in preparative photooxygenations. There is evidence that $C_{60}$ can also act as a sensitizer in aqueous systems [Orfanopoulos, M. and Kambourakis, S.: *Tetrahedron Letters* 36 (1995) 435–438]. Today $C_{60}$ is readily commercially available (e.g. Aldrich, USA). None of the foregoing, however, is directed, as this invention, towards the inactivation of enveloped viruses in the presence of $C_{60}$ and oxygen when irradiated with visible light.

It is well known that enveloped viruses can be inactivated by the action of singlet oxygen ($^1O_2$). Many different dyes are used to produce $^1O_2$ in virus inactivation studies [*Blood Cells* 18 (1992) 1–166; Mohr, H., Lambrecht, B., and Selz, A.: *Immunological-Investigations* 24 (1995) 73–85]. Enveloped viruses exposed to light in the presence of hypericin or rose bengal showed a loss of infectivity. Additionally the photodynamic inhibition of the viral fusion process in vesicular stomatitis, influenza and Sendai virus was observed due to a cross-linking of viral membrane proteins [Lenard, J., Rabson, A., and Vanderoef, R.: *Proc. Natl. Acad. Sci. USA* 90 (1993) 158–162; Lenard, J. and Vanderoef, R.: *Photochem. Photobiol.* 58 (1993) 527–531]. Singlet oxygen can react with aromatic and sulfur-containing amino acids but reacts principally with histidine residues in proteins.

The inventors of the present invention found that buckminsterfullerene ($C_{60}$), which is a potent generator of singlet oxygen, is useful for producing $^1O_2$ for the inactivation of enveloped viruses. In the present invention an inactivation capacity of the new photosensitizer $C_{60}$ in combination with visible light was found.

Although the invention was demonstrated with two different model viruses (vesicular stomatitis virus, VSV and Semliki Forest Virus, SFV) it is obvious for a person skilled in the art that the inactivation process according to the invention works also for other viruses. The tested viruses showed a loss of infectivity of more than 7 $\log_{10}$ $TCID_{50}$ (tissue culture infection dose) per ml when irradiated up to 5 hours in the presence of $C_{60}$. The presence of bovine serum albumin (BSA) during the irradiation barely slowed the inactivation. It has to be mentioned that many parameters involved in the photodynamic inactivation process are not yet fully optimized (e.g. stirring process, light source, supply of oxygen during the irradiation and most important, the formation of highly disperse suspensions of $C_{60}$). Therefore it is very likely that an even higher inactivation capacity and faster kinetics of the inactivation process may be found under optimized conditions.

Buckminsterfullerene is insoluble in aqueous solutions and is extremely stable. Therefore, in contrast to other photosensitizers (e.g. methylene blue), it is possible to recycle $C_{60}$ from the inactivation material. $C_{60}$ can be removed from the liquid by simple filtration; other separation methods can be advantageous if the material to be inactivated is a suspension. Since it is possible to synthesize carbon cages loaded with other molecules (e.g. iron) [Edelmann, F. T.: *Angew. Chem. Int. Ed.* 34 (1995) 981–985], it is also suggested to introduce special properties (e.g. magnetism) into the photosensitizer used in the present invention. The use of such filled molecules represents a preferred embodiment of the present invention because the filled photosensitizer can be more easily removed from the virus-inactivated suspensions than are photosensitizers without filling. The reuse of the $^1O_2$ generator is of great importance for economic purposes. The removal of the sensitizer also helps to exclude any toxic or undesirable complications. The very high singlet oxygen yield and the inertness to photooxidative destruction suggest great potential for photodynamic action in biological systems.

Buckminsterfullerene is able to generate $^1O_2$ in a photodynamic process which leads to the inactivation of enveloped viruses. $C_{60}$ is thus useful as a photosensitizer in virus inactivations by singlet oxygen in biological fluids (e.g. in blood products).

FIG. 1 is a diagram showing the kinetics of a photodynamic inactivation of Semliki Forest Virus (SFV) by buckminsterfullerene ($C_{60}$) according to example 1 of the invention.

A sample spiked with SFV was co-irradiated with $C_{60}$ under constant stirring and $O_2$ bubbling with visible light (●). Controls include the incubation of SFV with $C_{60}$ without irradiation (▽) and the irradiation of SFV without $C_{60}$ (O).

FIG. 2 is a diagram showing the effect of proteins on the inactivation kinetic according to example 2.

A sample spiked with SFV was co-irradiated with $C_{60}$ with no bovine serum albumin (BSA) (●) and with 2% bovine serum albumin (BSA) added prior to the irradiation with visible light (■).

Figure 1:
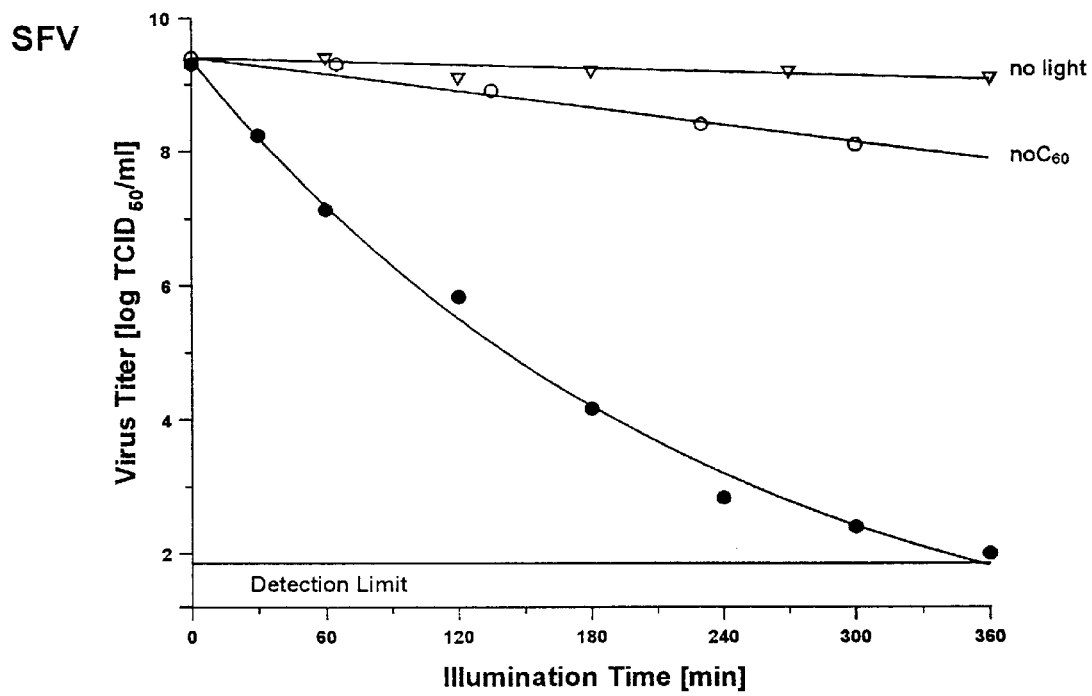

EXAMPLE 1:

A suspension of buckminsterfullerene ($C_{60}$; Aldrich, USA) was 10 obtained by sonification with a sonifier converter tip (sonifier model 110; Branson inc., USA) for approximately 5 minutes (position 3, 3 amps. D.C.). The $C_{60}$-suspension (1 mg/ml) in MBS (morpholinoethane-sulfonic acid buffered saline; 400 mOsm, pH 7.4) was spiked with Semliki Forest Virus (SFV, Togaviridae) to obtain a starting virus titer of approx. $10^9 TCID_{50}$ per ml (tissue culture infection dose). $O_2$ saturation of the stirred virus-$C_{60}$ suspension (in MBS containing 10% MM-Medium) was achieved by a constant flow of $O_2$ (bubbling) 5 minutes prior to and during the irradiation.

SFV was propagated in mosquito larvae cells (Aedes cells; clone C6/36, grown at 28° C. in Mitsuhashi-Maramorosch medium (MM-medium; Amimed, Switzerland), containing 16% FCS and supplemented with 100 mg streptomycin and 100 U penicillin per ml). Virus titers were determined on african green monkey kidney cells (Vero) by end point titrations according to established methods.

Photoirradiation of the stirred virus suspensions (2.3 ml, on ice) in a 1 cm glass cuvette containing 1 mg $C_{60}$ per ml was performed with a 350 W short arc mercury lamp (HBO 350 W; Osram, Germany) equipped with a 495 nm long pass filter (GG 495; Schott, Germany). To determine the kinetics of SFV inactivation 70 μl samples were taken after different irradiation times. $C_{60}$ was removed by centrifugation and residual virus was determined by endpoint titration of 10 fold serial dilutions.

To detect the infectivity of SFV, Vero cells, grown at 37° C. in RPMI 1640 medium (Seromed, Switzerland), containing 10% FCS and supplemented with 100 mg streptomycin and 100 U penicillin per ml) grown to 80–100% confluency on 96-well tissue culture plates (TPP, Switzerland) were infected with 50 μl probes of 1 in 10 serial dilutions in RPMI-medium of virus samples (8 wells per dilution). After incubation for three days at 37° C. in 5% $CO_2$, cytopathic effects (cell destruction) were visualized by staining the remaining cells with crystal violet (0.5% in methanol; Fluka, Switzerland). Virus titers were calculated according to the method of Spearman and Karber and indicated as $log_{10}$ ($TCID_{50}$).

FIG. 1 shows the time-dependent decrease of infectivity of SFV when irradiated with visible light in the presence of the photosensitizer buckminsterfullerene ($C_{60}$). The indicated points represent mean values of three independent experiments (filled circles). For control purposes, SFV was irradiated without $C_{60}$ (open circles), or incubated with 1 mg $C_{60}$ per ml at 4° C. without irradiation (open triangles) [Irradiation with visible light (●). Controls include the incubation of SFV with $C_{60}$ without irradiation (▽) and the irradiation of SFV without $C_{60}$ (O)]. The observed maximal nonspecific inactivation was in the range of one $log_{10}$ during five hours. The observed loss of infectivity of SFV ($TCID_{50}$) was in the range of 7 $log_{10}$ when irradiated for 5 hours or 5 $log_{10}$ when irradiated for 3 hours respectively.

EXAMPLE 2:

Since the virus inactivation by singlet oxygen is to be used in biological fluids, the effect of the presence of proteins during the photoinactivation was tested.

Figure 2:
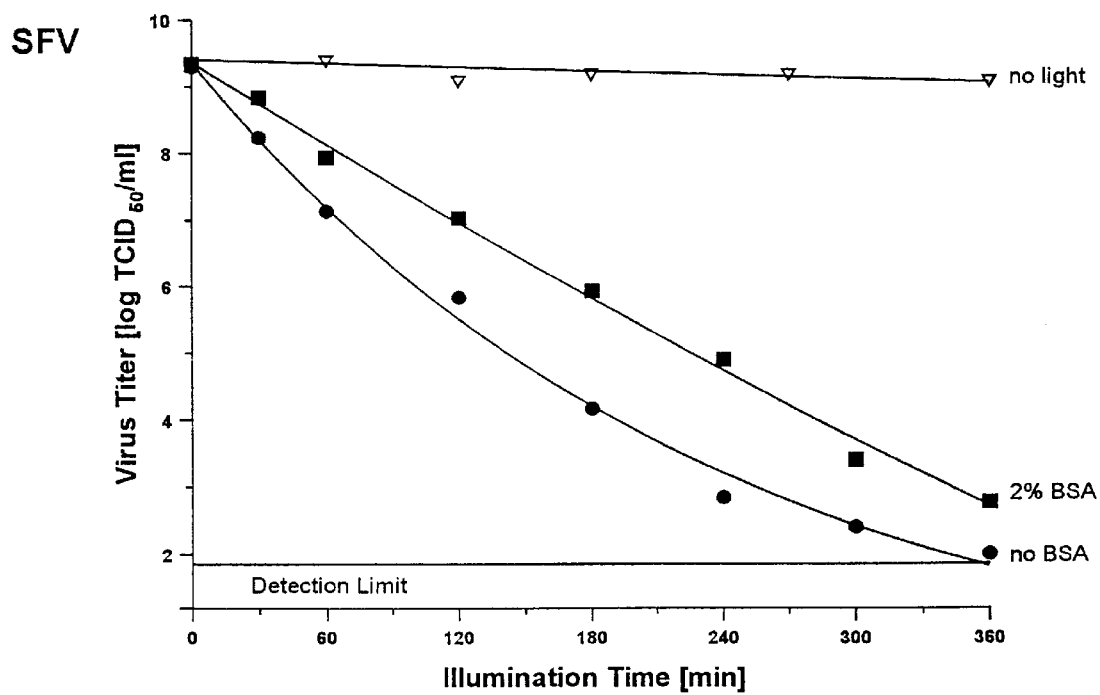

A suspension of $C_{60}$ containing 2% BSA (in MBS) was spiked with stock SFV (see example 1) [with no bovine serum albumin (BSA) (●) and with 2% bovine serum albumin (BSA) added prior to the irradiation with visible light (■)]. This suspension was irradiated under the same conditions as for example 1 (in MBS, 10% MM-medium≅0.1–0.2% protein, 2% BSA). A slightly slower virus inactivation kinetic was observed when 2% BSA was present in the SFV-$C_{60}$ suspension (FIG. 2, filled squares).

Figure 3:
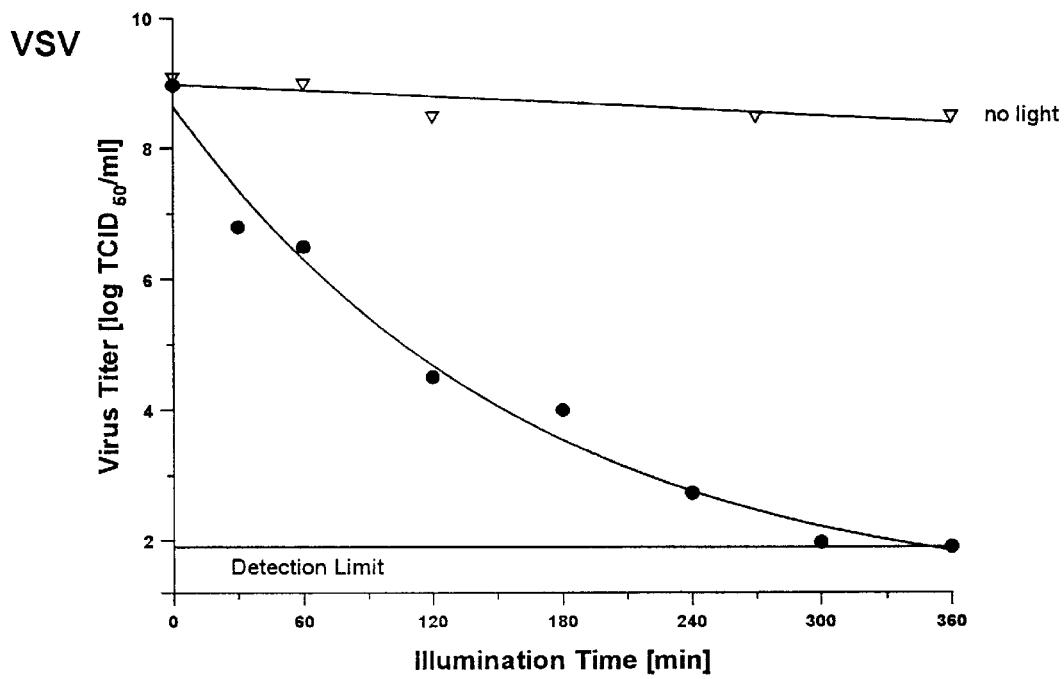
FIG. 3 is a diagram showing the kinetics of the photodynamic inactivation with Buckminsterfullerene of a sample spiked with vesicular stomatitis virus according to example 3.

EXAMPLE 3:

In an additional set of experiments (performed as in example1), the $C_{60}$ mediated photoinactivation of vesicular stomatitis virus (VSV; Rhabdoviridae) was tested. Mean values of three independent experiments are shown in FIG. 3 (filled circles ●). The nonspecific elimination or inactivation of VSV, when incubated with $C_{60}$ without irradiation, was less than one $log_{10}$ during five hours (open triangles ▽). As the stock-virus titer for VSV is lower than for SFV, the final concentration of MM-medium is 45%. This corresponds to a protein concentration of 0.5 to 1% in the suspension being inactivated.

Therefore, VSV showed a loss of infectivity of more than 7 $log_{10}$ when irradiated with visible light up to 5 hours in the presence of the singlet oxygen producing agent buckminsterfullerene even in the presence of proteins (0.5–1%).

Figure 4:
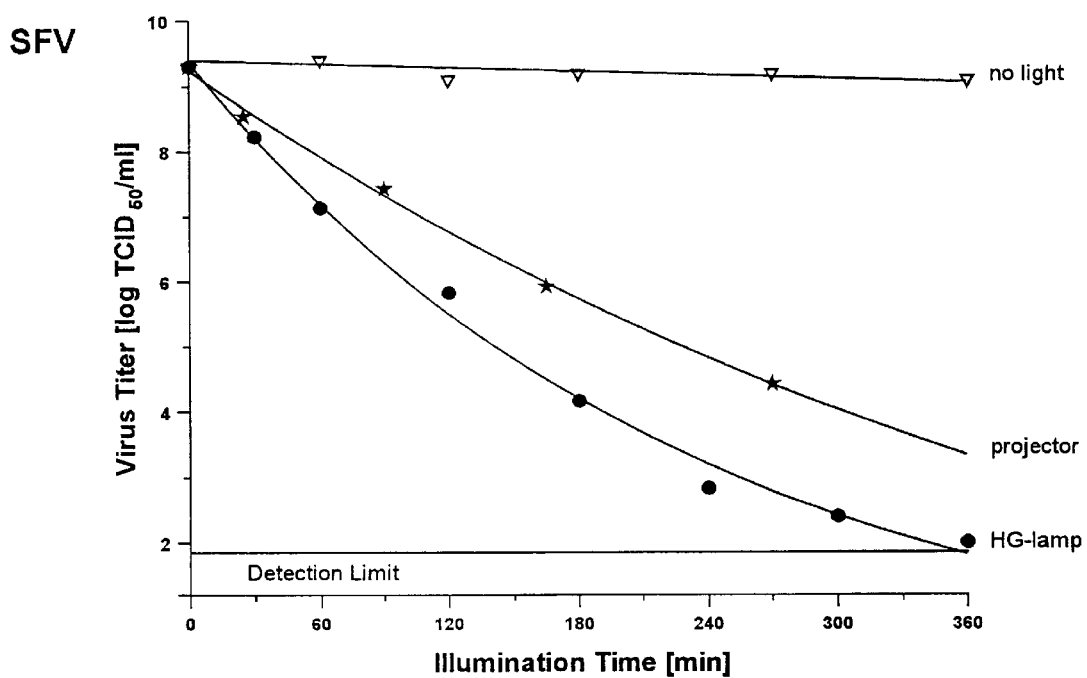
FIG. 4 is a diagram showing the effect of alternative light sources on the inactivation kinetic SFV according to example 4; the sample was irradiated with visible light in the presence of $C_{60}$ with a Hg-lamp (●) or two slide projectors respectively (★).

EXAMPLE 4:

To test other light sources for the production of $^1O_2$, SFV was co-irradiated with a suspension of $C_{60}$ (1 mg/ml; produced as in example1) with two slide projectors, equipped with a 420 nm long pass filter (GG 420; Schott, Germany), as light sources. It was found that SFV could be inactivated with a slower kinetic than observed with the Hg-lamp used in example 1 (FIG. 4; filled stars) [the sample was irradiated with visible light in the presence of $C_{60}$ with a Hg-lamp (●) or two slide projectors respectively (★)]. Therefore, it was shown that other light sources can be used for the production of singlet oxygen by $C_{60}$ (e.g. slide projector).

What is claimed is:

1. A process for inactivating enveloped viruses in an aqueous solution or an aqueous dispersion of material derived from the human body or from the bodies of animals comprising the steps of:

contacting the solution or dispersion with buckninsterfullerene as a photosensitizer;

saturating the solution or dispersion with oxygen; and irradiating the solution or dispersion with visible or invisible light which activates the oxygen into the singlet state for a time sufficient to inactivate the viruses contained in the solution or dispersion.

2. The process of claims 1, wherein the solution or dispersion of material derived from the human body or from the bodies of animals is human or animal plasma or a fraction thereof.

3. The process of claim 1, wherein the solution or dispersion of material derived from the human body or from the bodies of animals is a pharmaceutical composition comprising immunoglobulins or blood cells.

4. The process of claim 1, wherein the solution or dispersion is saturated with oxygen by blowing oxygen or a gas containing oxygen into the solution or dispersion; and wherein the irradiation is simultaneous with the blowing of oxygen or a gas containing oxygen.

5. The process of claim 4, wherein irrradiating and blowing is continued for 3 to 6 hours.

6. The process of claim 1, wherein the process is carried out continuously within a production line for manufacturing a pharmaceutical composition.

7. The process of claim 1, wherein the visible or invisble light has a wavelength in the range of 100 to 1000 nm.

8. The process of claim 1, wherein an antibody against the virus to be inactivated is added to the solution or suspension.

9. The process of claim 1, wherein the visible or invisible light has a wavelength in the range of 400 to 600 nm.

10. A process for inactivating enveloped viruses in an aqueous solution or an aqueous dispersion of material derived from the human body or from the bodies of animals comprising the steps of:

contacting the solution or dispersion with buckminsterfullerene as a photosensitizer;

saturating the solution or dispersion with oxygen; and irradiating the solution or dispersion with visible or invisible light which activates the oxygen into the singlet state for a time sufficient to inactivate the viruses contained in the solution or dispersion; and removing the buckminsterfullerene and optionally reusing it for one or more further inactivation processes.

11. The process of claim 10, wherein the solution or dispersion of material derived from the human body or from the bodies of animals is human or animal plasma or a fraction thereof.

12. The process of claim 10, wherein the solution or dispersion of material derived from the human body or from the bodies of animals is a pharmaceutical composition comprising immunoglobulins or blood cells.

13. The process of claim 10, wherein the solution or dispersion is saturated with oxygen by blowing oxygen or a gas containing oxygen into the solution or dispersion; and wherein the irradiation is simultaneous with the blowing of oxygen or gas containing oxygen.

14. The process of claim 13, wherein irrradiating and blowing is continued for 3 to 6 hours.

15. The process of claim 10, wherein the process is carried out continuously within a production line for manufacturing a pharmaceutical composition.

16. The process of claim 10, wherein the visible or invisible light has a wavelength in the range of 100 to 1000 nm.

17. The process of claim 10, wherein an antibody against the virus to be inactivated is added to the solution or suspension.

18. The process of claim 10, wherein the visible or invisible light has a wavelength in the range of 400 to 600 nm.

19. A process for inactivating enveloped viruses in an aqueous solution or dispersion of material derived from the human body or from the bodies of animals comprising the steps of:

contacting the solution or dispersion with buckminsterfullerene as a photosensitizer, wherein the buckminsterfullerene contains ferromagnetic particles;

saturating of the solution or dispersion with oxygen; irradiating the solution or dispersion with visible or invisible light which activates oxygen into the singlet state; and removing the buckminsterfullerene containing ferromagnetic particles; and optionally reusing it for one or more further inactivation processes.

20. The process of claim 19, wherein the solution or dispersion of material derived from the human body or from the bodies of animals is human or animal plasma or a fraction thereof.

21. The process of claim 19, wherein the solution or dispersion of material derived from the human body or from the bodies of animals is a pharmaceutical composition comprising immunoglobulins or blood cells.

22. The process of claim 17, wherein the solution or dispersion is saturated with oxygen by blowing oxygen or a gas containing oxygen into the solution or dispersion; and wherein the irradiation is simultaneous with the blowing of oxygen or gas containing oxygen.

23. The process of claim 22, wherein irrradiating and blowing is continued for 3 to 6 hours.

24. The process of claim 19, wherein the process is carried out continuously within a production line for manufacturing a pharmaceutical composition.

25. The process of claim 19, wherein the visible or invisble light has a wavelength in the range of 100 to 1000 nm.

26. The process of claim 19, wherein an antibody against the virus to be inactivated is added to the solution or suspension.

27. The process of claim 19, wherein the visible or invisible light has a wavelength in the range of 400 to 600 nm.

* * * * *